United States Patent [19]
Johnson

[11] Patent Number: 5,585,643
[45] Date of Patent: Dec. 17, 1996

[54] METHOD AND APPARATUS FOR DIRECTING ELECTRON RADIATION TO SUBCUTANEOUS CELLS

[76] Inventor: Jim H. Johnson, 394 Valley View Ave., San Jose, Calif. 95127

[21] Appl. No.: 421,507

[22] Filed: Apr. 12, 1995

[51] Int. Cl.⁶ ........................................ A61N 5/01
[52] U.S. Cl. .................. 250/492.3; 600/1; 600/3
[58] Field of Search ............... 250/492.3; 600/1, 600/3

[56] References Cited

U.S. PATENT DOCUMENTS

| | | | |
|---|---|---|---|
| 2,018,599 | 10/1935 | Brasch | 250/492.3 |
| 4,314,158 | 2/1982 | Lucido | 250/492.3 |
| 5,073,913 | 12/1991 | Martin | 378/34 |
| 5,144,647 | 9/1992 | Kikuchi | 378/153 |
| 5,190,516 | 3/1993 | Bronn | 600/1 |
| 5,216,255 | 6/1993 | Weidlich | 250/492.3 |
| 5,317,164 | 5/1994 | Kurokawa | 250/492.3 |
| 5,360,666 | 11/1994 | Eichmiller | 428/327 |

OTHER PUBLICATIONS

W. E. Dance, D. H. Rester, B. J. Farmer, J. H. Johnson and L. L. Baggerly, "Bremsstrahlung Produced in Thick Aluminum and Iron Targets by 0.5 to 2.8 MeV Electrons", *Journal of Applied Physics*, May 1968, vol. 39, No. 6, pp. 2881–2889.

D. H. Rester and W. E. Dance, "Bremsstrahlung Cross–Section Measurements at Incident Electron Energies of 1.0, 1.7, and 2.5 MeV", *Physical Review*, Sep. 5, 1967, vol. 161, No. 1, pp. 85–93.

D. H. Rester and W. E. Dance, "K–Shell Ionization of Ag, Sn, and Au from Electron Bombardment", *Physical Review*, Second Series, Dec. 2, 1966, vol. 152, No. 1, pp. 1–3.

*Primary Examiner*—Jack I. Berman
*Attorney, Agent, or Firm*—Albert C. Smith

[57] ABSTRACT

The present invention provides a device for delivering an electron beam providing radiation treatment to subcutaneous cells. The device includes a hollow needle having a proximal and a distal end for respectively directing the electron beam therethrough. The proximal end of the needle is adapted for attachment to the source of the electron beam. A scattering target for the electron beam is also provided. The scattering target is adapted for positioning at the distal end of the hollow needle whereby the distal end of the hollow needle is capable of insertion directly to the subcutaneous cells for radiation treatment. The present invention also provides a system for providing electron radiation treatment directly to subcutaneous cells that includes a source of an electron beam of selectively variable content and energy levels effective for electron radiation treatment and a hollow needle with a scattering target as described above. The present invention also contemplates a method for providing electron radiation treatment directly to subcutaneous cells.

23 Claims, 7 Drawing Sheets
(6 of 7 Drawing(s) in Color)

METHOD AND APPARATUS FOR DIRECTING ELECTRON RADIATION TO SUBCUTANEOUS CELLS

FIELD OF THE INVENTION

The present invention relates generally to radiation therapy for treating malignant cells in humans and animals. The present invention relates specifically to a method and apparatus for directing electron radiation to the malignant cells while minimizing exposure to the surrounding healthy cells.

BACKGROUND OF THE INVENTION

The majority of radiation therapy uses $\chi$-radiation or $\gamma$-radiation produced by particle accelerators or radioactive sources. The electromagnetic radiation is highly penetrating to tissue and provides a radiation path straight through the body. All tissues in the path of the radiation beam are about equally exposed to the radiation which means that both the malignant mass and those healthy cells in front of and behind the malignant mass are irradiated.

Neither $\chi$-rays nor $\gamma$-rays themselves cause damage to cells. These radiations may pass through a body without any interaction at all; or they may interact with cells such as tissue, bone, or the like, anywhere along their path to produce energetic free electrons. The electrons carry a negative charge that moves through the tissue from the spot where they were produced to cause damage to each cell they interact with by stripping other electrons. The electrons give up energy with each interaction along their path until they come to a halt. The damage of otherwise healthy cells often causes adverse patient reaction to the radiation treatment.

A number of techniques have been attempted to avoid damaging healthy cells during radiation treatment. Radioactive sources of $\beta$-rays (electrons) and $\alpha$-particles have been used, but handling the radioactive material is a hazard to both patient and physician. Further, the range of particles from radioactive sources is fixed, often requiring a number of sources to obtain a result. Physically large, multimillion dollar particle accelerators have also been proposed in an effort to provide local irradiation to tumors. However, these devices are not practical for routine radiation therapy.

Another technique that attempts to minimize damaging cells during radiation treatment is disclosed in U.S. Pat. No. 5,190,516 as intraoperative radiotherapy. This technique involves a more direct application of the treatment beam directly to an internal treatment surface which has been exposed temporarily dining the course of a surgical procedure. Intraoperative radiotherapy, however, usually requires moving a patient from an operating room to a radiotherapy suite during surgery or providing an expensive operating theatre in a radiotherapy facility. Alternatively, the treatment beam must be transported from the source to the operating room through a well-shielded, expensive and complex beam transport system.

Accordingly, the need exists for a comparably inexpensive means of introducing the electrons directly to the site of the malign an cy and limit the range of the electrons so that they only penetrate to a desired depth and configuration Avoiding irradiation of the healthy tissue in front of and surrounding the malignant mass provides a marked reduction in damage to otherwise healthy cells. A result of introducing energetic electrons to a tumor site and controlling the energy and spatial distribution to only cover the volume around the malignant mass as defined by the radiation therapist could significantly improve the patient's reaction to conventional radiation therapy.

SUMMARY OF THE INVENTION

In accordance with the present invention, a device is provided for delivering an electron beam from a source providing radiation treatment to subcutaneous cells. The device includes a hollow needle having a proximal and a distal end for respectively directing the electron beam therethrough. The proximal end of the needle is adapted for attachment to the source of the electron beam. A scattering target for the electron beam is also provided. The scattering target is adapted for positioning at the distal end of the hollow needle whereby the distal end of the hollow needle is capable of insertion directly to the subcutaneous cells for radiation treatment. Preferably, an 18-gauge biopsy needle is used as the hollow needle.

The present invention also provides a system for providing electron radiation treatment directly to subcutaneous cells. The system includes a source of an electron beam of selectively variable current and energy levels effective for radiation treatment and a hollow needle having a proximal and a distal end for respectively directing the electron beam therethrough. The system includes means for focusing the electron beam through the hollow needle and a scattering target for the electron beam. The target is adapted for positioning at the distal end of the hollow needle and is made of a material capable of scattering the electron beam without significantly reducing its energy. Preferably, the system also includes means for collimating the beam with an absorber having a small diameter hole on an access of the axis of the electron beam and means of steering the electron beam by locating the beam with a video camera observing the glow of the electron beam as it strikes a lead phosphide screen.

The present invention also contemplates a method for providing electron radiation treatment directly to subcutaneous cells. The method includes the steps of: generating an electron beam of selectively variable current and energy levels effective for electron radiation treatment; inserting a hollow needle to position the distal end of the hollow needle in proximity to the subcutaneous cells pre-determined to require radiation treatment; and, directing the electron beam through the hollow needle and through a scattering target at the distal end of the hollow needle to scatter electrons in the proximity of the subcutaneous cells.

BRIEF DESCRIPTION OF THE DRAWINGS

The file of this patent contains at least one drawing executed in color. Copies of this patent with color drawing(s) will be provided by the Patent and Trademark Office upon request and payment of necessary fee.

DESCRIPTION OF THE PREFERRED EMBODIMENT

Figure 1:
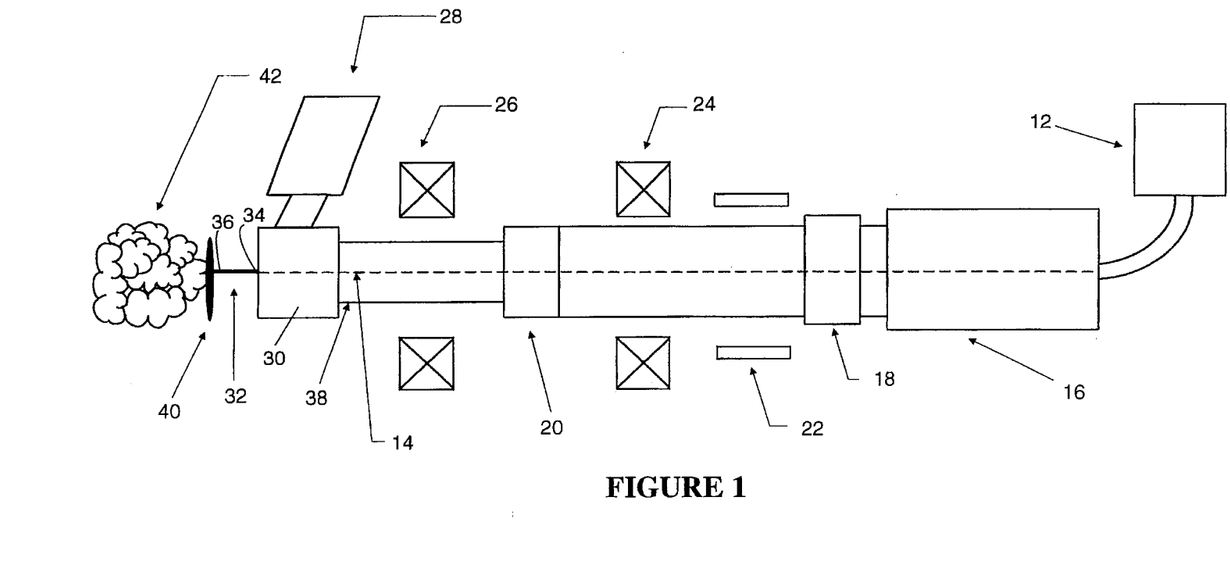
FIG. 1 is a schematic of one embodiment of the present invention for providing radiation treatment to subcutaneous cells.

In accordance with the present invention, FIG. 1 is a schematic of the system 10 for providing radiation treatment directly to subcutaneous cells. The system 10 includes a source 12 of energetic electrons for a beam 14 having selectively variable current and energy levels effective for electron radiation treatment controlled by a linear accelerator 16. The system 10 includes a collimator 18 for collimating the electrons into a beam 14 preferably having a diameter of about 0.040 inches. A suitable means of collimating the electrons is to use an absorber with a small diameter hole on the axis of the beam 14. More than one collimator, such as 20, may be used to collimate the beam 14 to the pre-determined diameter.

The system 10 also includes a focusing lens 22 and at least one set of steering coils 24 for steering the beam 14. A suitable meters for focusing the beam 14 is a pair of quadruple lenses. A second set of steering coils 26 may be used to finely control the position of the beam 14. A suitable means of steering the electron beam 14 are an orthogonal pair of magnetic lenses. The system may also includes a video camera 28 for observing the glow of the beam 14 as it strikes a lead phosphide screen 30 or other means for illuminating the beam 14. The video camera 28 is a suitable means for locating the beam 14 to assist in steering the beam 14.

The system 10 includes a hollow needle 32 having a proximal end 34 and a distal end 36. The proximal end 34 is adapted to mount to the end of the accelerator beam tube 38 and receives the beam 14 therethrough. A suitable means for mounting the proximal end 34 is a helioarc weld. At the distal end 36 of the needle is affixed a target 40 for scattering the beam 14 in a predetermined pattern of scattered electrons 42.

Preferably, the needle 32 is an 18 gauge biopsy needle that is rigid with a straight length of about 6 inches and has an interior diameter of about 50 mils or about 50 thousandths of an inch. Accordingly, the collimated electron beam 14 has a diameter less than the interior diameter of the needle 32. The needle 32 is made of metal which reflects the electrons passing therethrough and funnels the electrons toward the distal end 36. It is preferred that the needle 32 is rigid since a flexing needle may distort the path of the electron beam 14.

Figure 2:
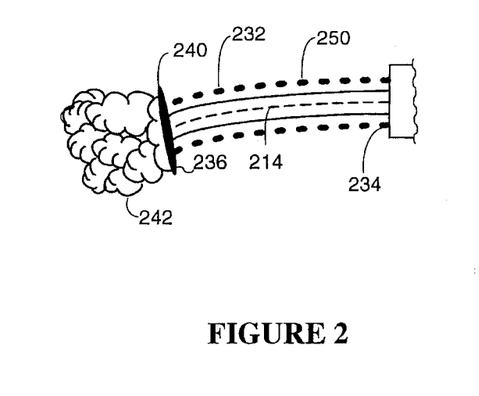
FIG. 2 is an isolated, cross-section view of another embodiment of the hollow needle provided by the present invention.

Referring to FIG. 2, another embodiment of the hollow needle 232 having a curved configuration is illustrated for receiving an electron beam 214 at the proximal end 234. The electron beam 214 is directed along the configuration by external steering means such as a series of magnets 250 which substantially extend along the length of the needle 232. Each one of the magnets 250 encircles the circumference of the needle 232. The magnets 250 create a magnetic field through which passes the electron beam 214. The magnetic field generated by the magnets 250 extends along a substantial length of the needle 232 to control the electron beam 214. The electron beam 214 also reflects off the interior walls of the needle 232 to tunnel toward the distal end 236.

Preferably, the scattering target 40 is a metallic disc capable of scattering the electrons in a pre-determined configuration and is affixed to the distal end 36 of the needle in a generally perpendicular position to the needle. The thickness of the target 40 is in the range of about 0.002 inch to about 0.038 inch when aluminum or tin is used at an electron beam energy of about 2 to 3 million electron volts. The atomic number of the metal, the energy of the electron beam and the thickness of the target 40 determine the configuration of the electron scatter as the beam impinges the target 40. The scattered electrons will emerge into the treatment area to fill the volume defined by the therapy. The target material is selected for its scattering ability at the energy level of the electron beam selected for the treatment. For example, at 2 MeV a 0.012 inch aluminum target produces a hemispherical radiation volume of 0.4 inch diameter, while at 12 MeV a thicker, heavier metal would be required to produce a 2.5 inch diameter hemisphere.

In operation, the present invention provides a radiation treatment directly to subcutaneous cells. The inventive method includes generating an electron beam of selectively variable current and energy levels effective for electron radiation treatment. As described above, the hollow needle 32 is inserted through the subject's skin so that the distal end of the hollow needle is in proximity to the subcutaneous cells pre-determined to require radiation treatment. The electron beam 14 is directed through the hollow needle 32 and through the scattering target 40 at the distal end of the hollow needle to scatter electrons in the proximity of the subcutaneous cells.

There are many suitable means for steering of electron beam 14 into the proximal end of the hollow needle 32. Generating an electron beam 14 may include collimating and focusing the electron beam. The method may also include the step of locating the electron beam visually to steer the beam into the proximal end of the hollow needle. Preferably, the hollow needle is evacuated prior to the directing step. Directing the electron beam may include controllably removing the hollow needle from the proximity of the subcutaneous cells while the electron beam is still being directed through the hollow needle.

EXAMPLES

Approximately 50 Giant New Zealand rabbits were irradiated in accordance with the present invention. Doses up to 5000 rads were used to determine the pattern of cell damage to various organs. The versatility of the invention was demonstrated by including the liver, pancreas, spleen, brain, and the interior of the bone.

A 3 million volt Van de Graff accelerator was used as the source of electrons. As described above, a series of control devices was employed to produce and direct the beam of electrons through the biopsy needle to the metallic target foil on the end of the accelerator. The foil was selected to produce a scattered beam in tissue of hemispherical shape of approximately 0.4 inches in diameter. The energy of the electron beam was provided by the generating voltmeter in the accelerator. Calibration of the meter was achieved through the use of Si(Li) detectors to determine the energy of electrons elasticity scattered by thin foils of aluminum inserted in the beam. Reference to the 625-keV internal conversion line from a $Cs^{137}$ source and the 482-keV, 972 keV, and 1.680 MeV lines from a $Bi^{207}$ source provided the energy calibration for the solid-state detector.

The approximate dose delivered to the subject animal was determined by two methods. The first was done by measuring the accelerator beam current by intercepting it with a Faraday Cage inserted into the beam just prior to its entering the needle. The total charge deposited was determined by removing the Faraday Cage and allowing the irradiation to occur for a measured period of time.

The second method, which was used simultaneously with the first during each irradiation, used the animal as a Faraday Cage. The accumulated charge deposited in the animal during the irradiation was measured with an Elcor Model 309A current integrator. The energy deposited per gram in the irradiated hemisphere was calculated using the dE/dX of electrons of this energy in carbon. To avoid errors due to leakage of charge to ground by any paths other than through the meter, the table on which the animal was lying was insulated from ground and a thin insulating film was applied to the biopsy needle to isolate it from the animal. The accumulated charge using both methods correlated by better than 5%. The largest errors in dose deposited were due to the assumptions that the energy was deposited uniformly in a hemisphere of 0.4 inch diameter and that all electrons were restricted to that volume. In order to obtain the desired result, which was to determine the extent of control of the electron beam, a calculated dose of 5000 rads was used for each irradiation. The measured dose dropped from about 5000 rads to about one rad within the distance of 0.4 inch. It was expected that this would produce a region of destroyed cells completely surrounded by healthy cells, when examined in the Pathology Lab.

Because the laboratory was not equipped with a means of externally viewing the placement of the needle in the animal, each subject was anesthetized and an incision was made by the surgeon, exposing the site to be irradiated. The animal was moved into position on the needle and supported appropriately. The procedure was quick and the total irradiation time was of the order of 1 minute. The wound was sutured, if necessary, and the animal was returned to its cage.

The subject animals were maintained after irradiation at the Baylor Medical Center in Dallas. No subjects were lost due to the irradiation. All healed normally. A schedule for sacrificing the subject animals over a period of approximately 12 months was established.

RESULTS

Figure 3A:
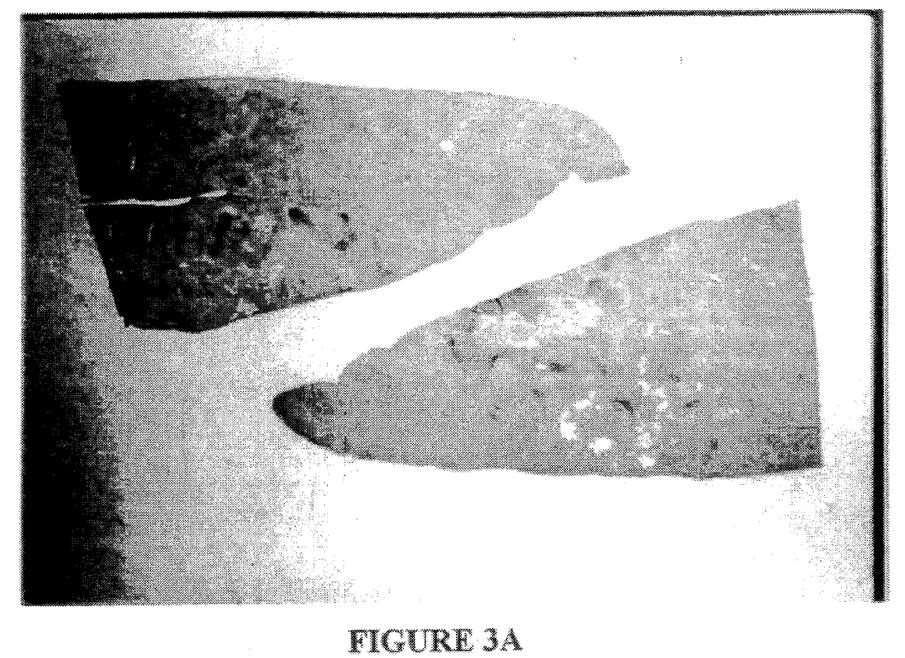
FIGS. 3A and 3B are cross section views of a liver of an animal subject treated in accordance with the present invention 6 weeks after irradiation.
Figure 3B:
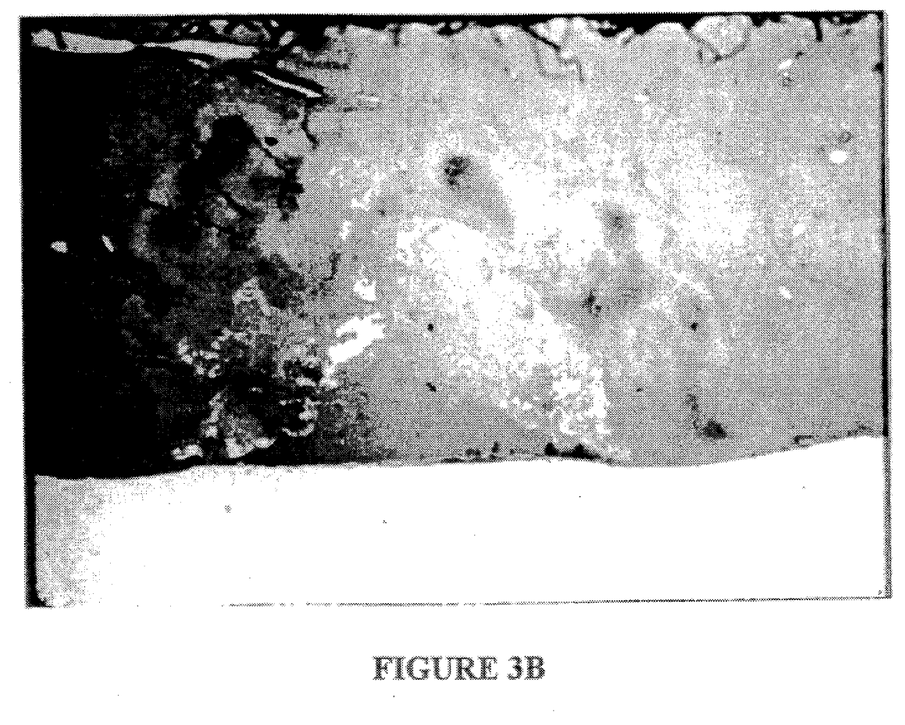

The irradiated tissue and surrounding area was removed from each animal subject in accordance with standard pathological procedures and slides were prepared by the team pathologist at Baylor for examination. Some of the samples were stained for easier viewing under the microscope. FIGS. 3A and 3B are cross section views of the liver from an animal sacrificed 6 weeks after irradiation. FIG. 3A illustrates the level of control obtained to limit the irradiated area and the details of the well-defined transition from the cells completely destroyed to the healthy cells. FIG. 3B shows a view under a microscope of the intended irradiated area being completely destroyed. The band separating totally destroyed cells from completely healthy cells, at this electron energy, is approximately 10 cell diameters.

Figure 4:
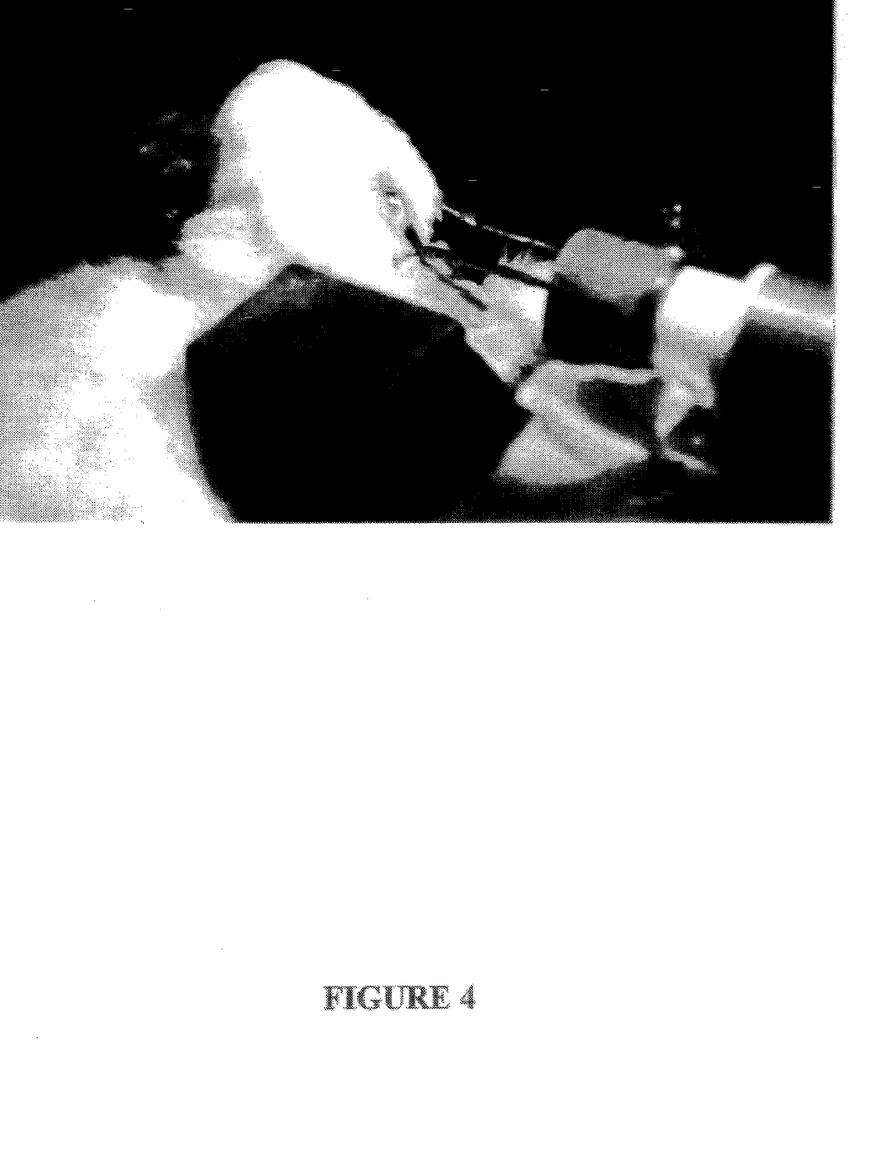
FIG. 4 illustrates an animal subject prepared for brain cell irradiation in accordance with the present invention.
Figure 5:
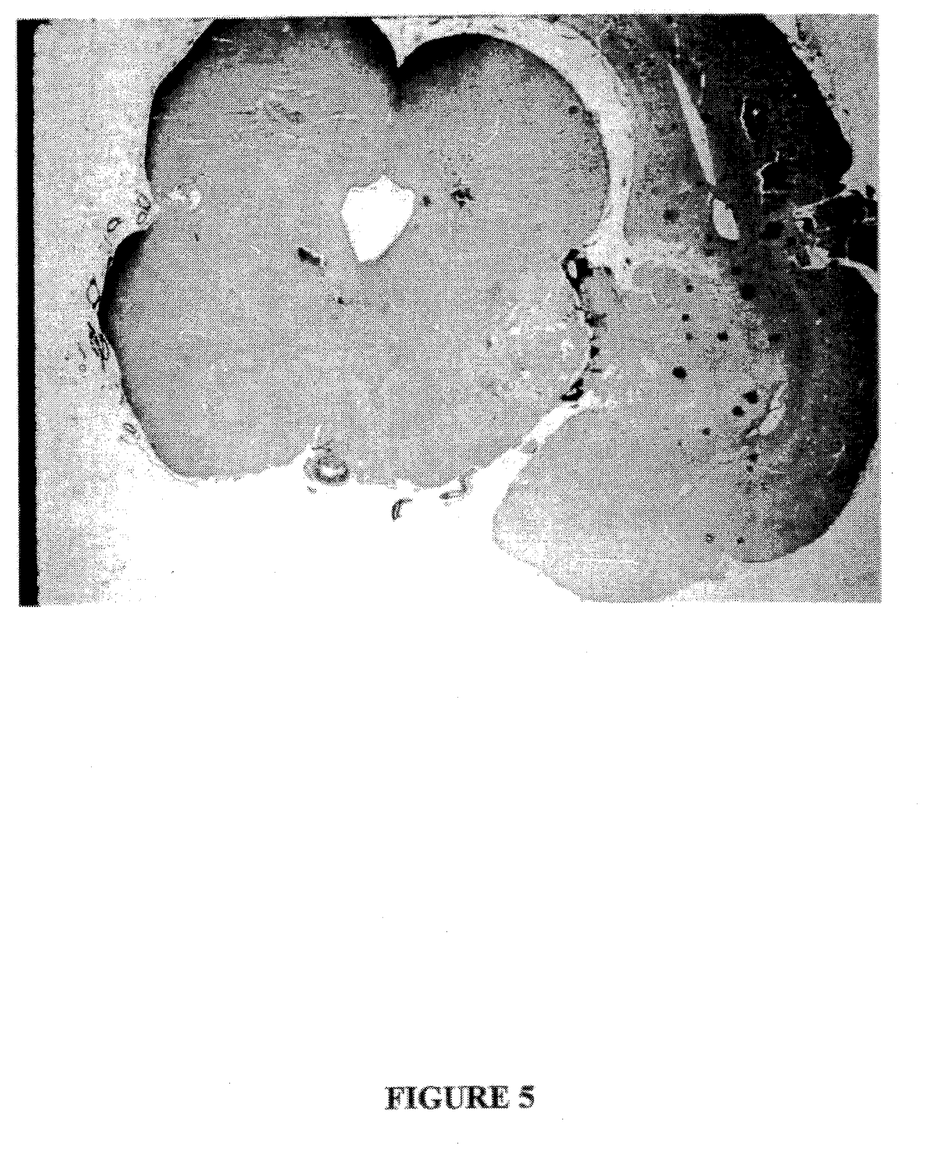
FIG. 5 is a cross-section view of an organ of an animal subject 6 weeks after irradiation in accordance with the present invention.

FIG. 4 shows a subject animal prepared for brain cell irradiation. FIG. 5 is the pathology slide at 6 weeks. Again the pattern of cell destruction is distinct and well defined.

Figure 6:
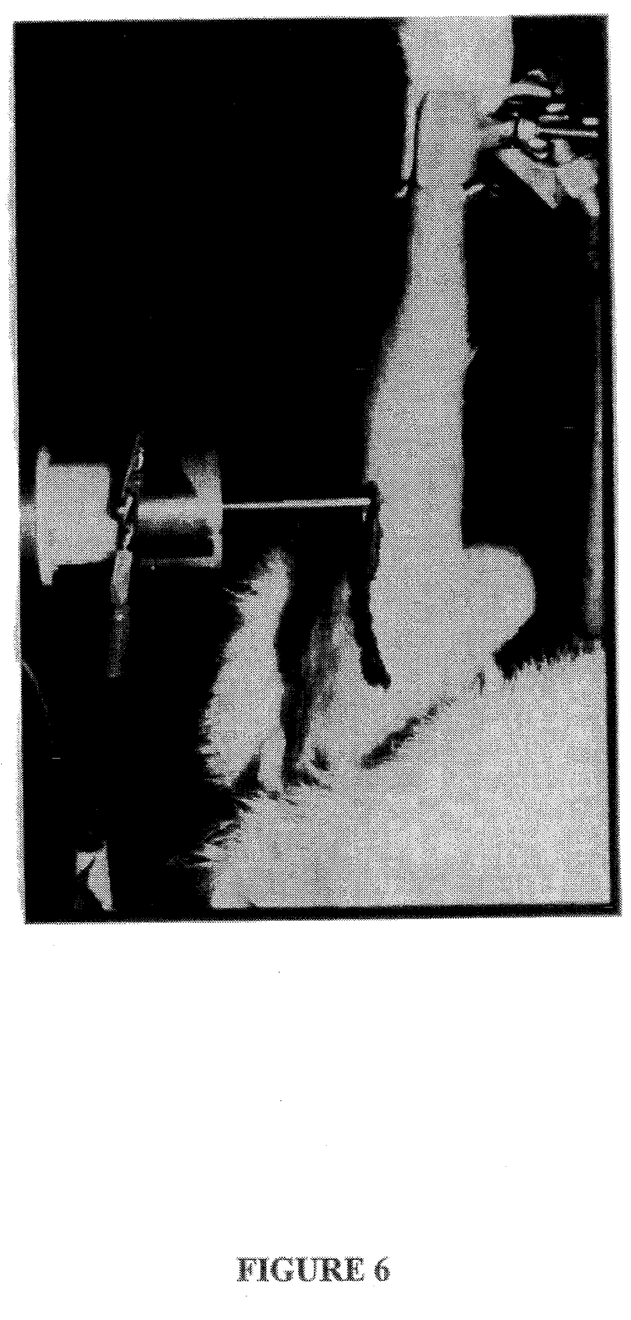
FIG. 6 illustrates an animal subject prepared for irradiation of a leg bone in accordance with the present invention.
Figure 7A:
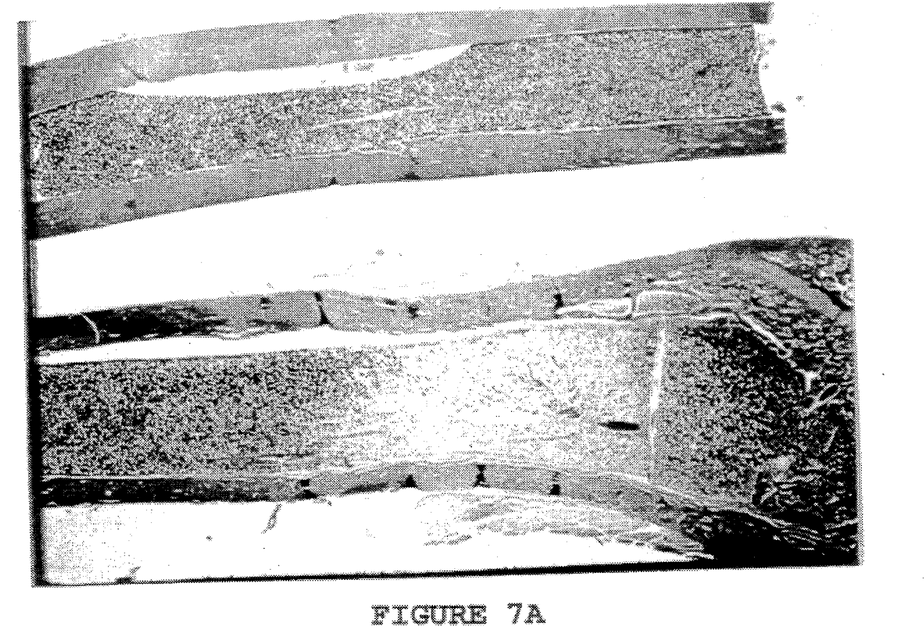
FIG. 7 is a cross section view of an irradiated bone from an animal subject in accordance with the present invention.
Figure 7B:
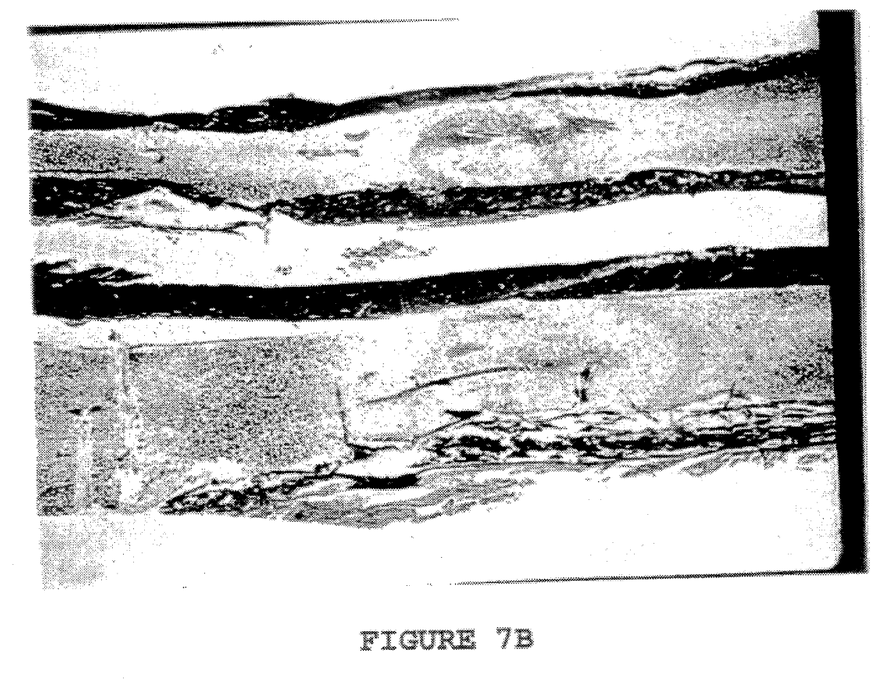

FIG. 6 shows the irradiation of the leg bone. In one case, the needle was firmly pressed against the outside of the bone. No tissue was exposed to the direct electron beam. In a second long bone study, the needle was inserted at the distal end of the femur and passed retrograde into the marrow chamber. The electron beam was then sent along the long axis. Doses as high as 10,000 rads were given and, as with other tissues, demarcation between dead and unaffected tissue was sharp. FIG. 7 shows samples of irradiated bone.

Figure 8:
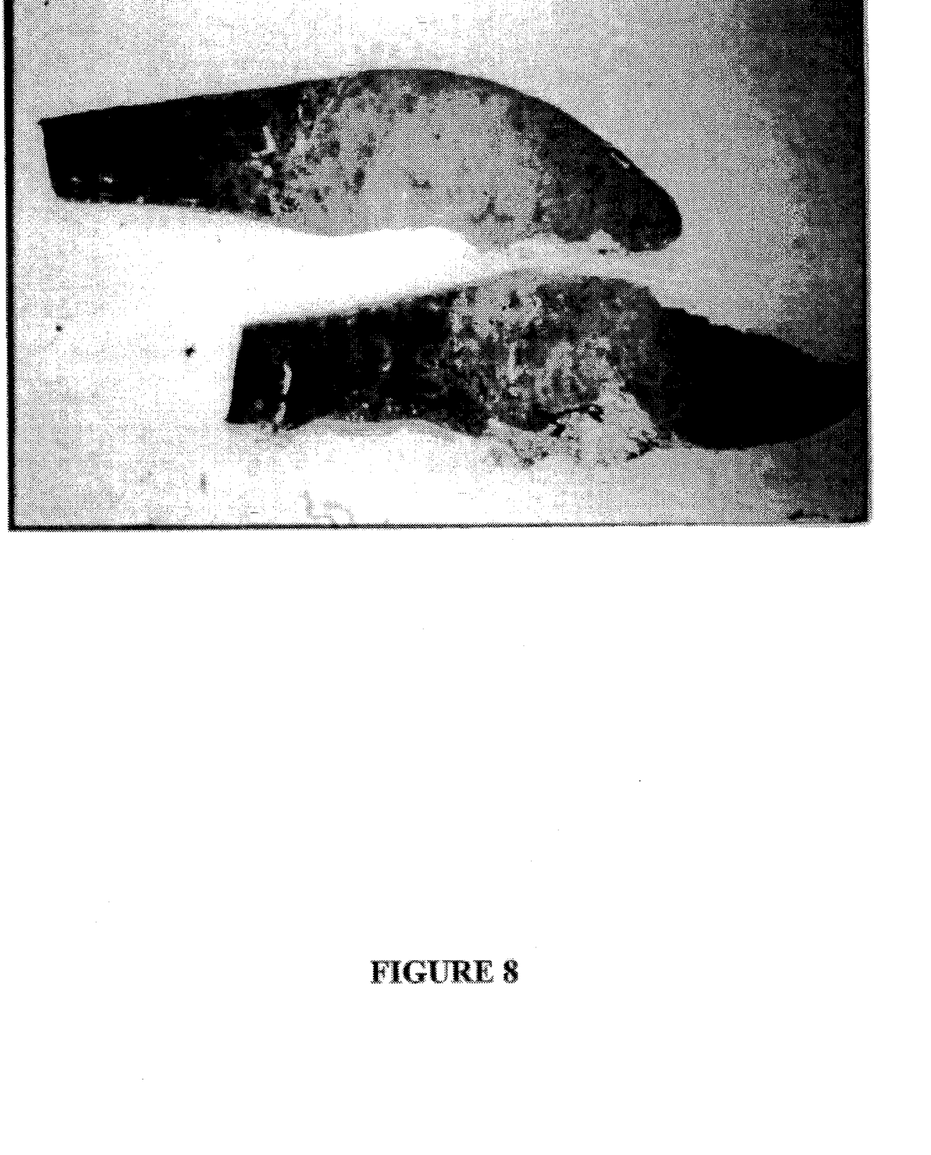
FIG. 8 is a cross section view of an irradiated spleen from an animal subject in accordance with the present invention.

Minimal periosteal changes and no muscle damage was noted. No pathologic fractures occurred at over 12 months. In fact, revascularization and recalcification of the bone matrix was evident. The present invention may be used in the treatment of osteogenic malignancies, since the present invention was able to deliver super lethal doses of ionizing radiation without the usual limiting factor of massive soft tissue damage. FIG. 8 is a sample of the irradiated spleen showing a pattern similar to the previous ones of cell destruction surrounded by healthy cells.

The examples demonstrate the ability of the present invention to pass a beam of megavolt electrons through an 18 gauge biopsy needle, scatter it into a controlled volume within a subject animal and confine the cell damage to the controlled volume. Results of the pathology examinations demonstrate the effectiveness of the present invention to irradiate a defined treatment area while avoiding irradiation of the surrounding healthy cells.

I claim:

1. A device for delivering an electron beam from a source providing radiation treatment to subcutaneous cells, the device comprising:

a hollow needle having a proximal end and a distal end for respectively directing the electron beam therethrough, the proximal end being adapted for attachment to the source of the electron beam, the distal end of the needle is capable of insertion directly to the subcutaneous cells for electron radiation treatment; and a scattering target for the electron beam, the target adapted for positioning at the distal end of the hollow needle in the path of the electron beam emerging from the needle, the scattering target is made of a material capable of scattering the electron beam without significantly reducing the energy of the beam.

2. The device of claim 1, wherein the device further includes means for evacuating the hollow needle during the electron radiation treatment as the electron beam passes therethrough.

3. The device of claim 1, wherein the needle includes metallic walls which provide for funneling of the electron beam to the distal end of the needle.

4. The device of claim 1, wherein the needle is curved.

5. The device of claim 1, wherein the needle has an interior diameter of about 50 mils.

6. The device of claim 1, wherein the scattering target is an aluminum disc having a thickness of about 2 to about 38 thousandths of an inch and the energy of the electron beam is about 2 to about 3 million electron volts.

7. The device of claim 1, wherein the scattering target is affixed to the distal end of the needle in a generally perpendicular position.

8. A system for providing radiation treatment directly to subcutaneous cells, the system comprising:

a source of an electron beam of selectively variable current and energy levels effective for radiation treatment;

a hollow needle having a proximal and a distal end for respectively directing the electron beam therethrough;

means for focusing the electron beam through the hollow needle; and a scattering target for the electron beam, the target adapted for positioning at the distal end of the hollow needle, the target made of a material capable of scattering the electron beam.

9. The system of claim 8, wherein the source includes means of collimating the electron beam.

10. The system of claim 9, wherein the collimating means includes an absorber with a small diameter hole on an access of the axis of the electron beam.

11. The system of claim 8, wherein the electron beam source includes means of steering the electron beam.

12. The system of claim 11, wherein the steering means includes an orthogonal pair of magnetic lenses.

13. The system of claim 11, wherein the steering means includes means of locating the electron beam prior to entering the proximal end of the hollow needle.

14. The system of claim 13, wherein the locating means includes a video camera observing the glow of the electron beam as it strikes an illuminating screen.

15. The system of claim 8, wherein the focusing means is a pair of quadruple lenses.

16. The system of claim 8, wherein the system includes means for accurately inserting the hollow needle in a patient.

17. The system of claim 8, wherein the scattering of the electron beam is well-defined within about 10 cell diameters between dead and healthy cells.

18. A method for providing radiation treatment directly to subcutaneous cells, the method including the steps of:

generating an electron beam of selectively variable current and energy levels effective for electron radiation treatment; inserting a hollow needle to position the distal end of the hollow needle in proximity to the subcutaneous cells pre-determined to require radiation treatment;

directing the electron beam through the hollow needle and through a scattering target at the distal end of the hollow needle to scatter electrons in the proximity of the subcutaneous cells.

19. The method of claim 18, wherein the step of directing the electron beam includes the steering of electron beam into the proximal end of the hollow needle.

20. The method of claim 19, wherein the step of generating an electron beam further includes the steps of:

collimating the electron beam; and focusing the electron beam.

21. The method of claim 18, whereby the method further includes the step of locating the electron beam visually to steer the beam into the proximal end of the hollow needle.

22. The method of claim 18, wherein the method further includes the step of evacuating the hollow needle prior to the directing step.

23. The method of claim 18, wherein after the step of directing the electron beam, the method includes the step of controllably removing the hollow needle from the proximity of the subcutaneous cells while the electron beam is still being directed through the hollow needle.

* * * * *